United States Patent
Wang et al.

(10) Patent No.: US 8,066,376 B2
(45) Date of Patent: Nov. 29, 2011

(54) DYNAMIC SHAPE DISCRIMINATION VISION TEST

(75) Inventors: Yi-Zhong Wang, Plano, TX (US);
William R. Krenik, Garland, TX (US)

(73) Assignee: Vital Art & Science Incorporated, Richardson, TX (US)

( * ) Notice: Subject to any disclaimer, the term of this patent is extended or adjusted under 35 U.S.C. 154(b) by 13 days.

(21) Appl. No.: 12/434,279

(22) Filed: May 1, 2009

(65) Prior Publication Data
US 2009/0273758 A1    Nov. 5, 2009

Related U.S. Application Data

(60) Provisional application No. 61/049,461, filed on May 1, 2008.

(51) Int. Cl.
*A61B 3/02* (2006.01)
*A61B 3/10* (2006.01)

(52) U.S. Cl. .................. 351/243; 351/205; 351/211

(58) Field of Classification Search .................. 351/243, 351/205, 211, 221, 246
See application file for complete search history.

(56) References Cited

U.S. PATENT DOCUMENTS

| | | | | |
|---|---|---|---|---|
| 5,883,692 | A * | 3/1999 | Agonis et al. | 351/224 |
| 7,367,675 | B2 * | 5/2008 | Maddalena et al. | 351/237 |
| 2003/0223038 | A1 * | 12/2003 | Alster et al. | 351/211 |
| 2010/0128222 | A1 * | 5/2010 | Donaldson | 351/210 |

OTHER PUBLICATIONS

Hess et al.; "Are judgements of circularity local or global?"; Vision Research 39 (1999) 4354-4360.
Jeffrey et al.; "Circular contour frequency in shape discrimination"; Vision Research 42 (2002) 2773-2779.
Loffler et al.; Local and global contributors to shape discrimination; Vision Research 43 (2003) 519-530.
Wilkinson et al.; Detection and recognition of radial frequency patterns; Vision Research 38 (1998) 3555-3568.
Wang; "Effects of Aging on Shape Discrimination"; Optometry Vision Science, vol. 78, No. 6, (2001) pp. 447-454.
Wang et al.; "Shape Discrimination in Age-Related Macular Degeneration"; Investigative Opthalmology & Visual Science, Jun. 2002, vol. 43, No. 6.
Wang et al.; Contributions of local orientation and position features to shape integration; Vision Research 45 (2005) 1375-1383.

* cited by examiner

*Primary Examiner* — Dawayne Pinkney (57) ABSTRACT

A vision testing system and method to assess vision function. In one embodiment, the vision testing system comprises: (1) a display; (2) a computer coupled to the display and configured to provide dynamic images, each including a substantially constant fixed point of fixation; and (3) a human input device coupled to the computer, wherein responses from a test subject are fed back to the computer to assess the test subject's vision function.

28 Claims, 8 Drawing Sheets

DYNAMIC SHAPE DISCRIMINATION VISION TEST

CROSS-REFERENCE TO RELATED APPLICATION

This application claims the benefit of U.S. Provisional Application Ser. No. 61/049,461, filed by Yi-Zhong Wang and Bill Krenik on May 1, 2008, entitled "Dynamic Shape Discrimination Vision Test," incorporated herein by reference.

TECHNICAL FIELD OF THE INVENTION

This application is directed, in general, to techniques for testing human vision function and, more specifically, to a system and method of to assess vision function using dynamic images that change at predetermined rates and alter their shapes in predetermined ways so that accurate assessment of retinal function and other vision function is possible.

BACKGROUND OF THE INVENTION

Retinal diseases are common, difficult to diagnose and track and can have very serious consequences. For example, macular degeneration is a very serious eye disease that affects up to roughly 20% of the elderly population and is the leading cause of blindness in the developed world. Many other retinal diseases such as glaucoma and diabetic retinopathy also affect large numbers of persons and can lead to serious loss of vision function. Due to the very serious nature of these diseases, it is highly regrettable that low cost and highly effective screening and disease tracking systems are not available. Today, the onset of retinal disease is very often first detected by patients noticing vision loss in their daily activity. Otherwise, paper grids referred to as Amsler grids are also used to provide a rudimentary low-cost screening tool. However, very often by the time it has been detected and diagnosed, considerable vision function has been lost and cannot be recovered. Additionally, changes in vision function for patients already diagnosed with retinal disease can signal the need for more aggressive or even emergency treatment. Hence, a low cost and effective system for screening for retinal disease and tracking retinal function is highly desirable. Accordingly, it is clear that vision function testing techniques to enable highly effective retinal function testing and other vision function testing are highly desirable.

Fortunately, computer graphics and gaming technology has now advanced to the level that low cost, highly effective devices for vision function testing and tracking can be envisioned. Binocular viewers allow each eye to be measured or trained independently or together, advances in variable optics allow for changes in focus to be accommodated, computer generated graphics allow interesting static and dynamic images to be created and low cost human input devices allow user feedback information to be collected easily concerning how a user is reacting to the given images.

SUMMARY OF THE INVENTION

To address the above-discussed deficiencies of the prior art, the invention provides, in one aspect, a vision testing system. In one embodiment, the vision testing system comprises: (1) a display; (2) a computer coupled to the display and configured to provide dynamic images, each including a substantially constant fixed point of fixation; and (3) a human input device coupled to the computer, wherein responses from a test subject are fed back to the computer to assess the test subject's vision function.

Another aspect of the invention provides a method to assess vision function. In one embodiment, the method to assess vision function comprises: (1) providing dynamic images, each including a substantially constant fixed point of fixation, to a test subject on a display of coupled to a computer; and (2) assessing the test subject's vision function based on responses from the test subject while viewing the dynamic images, the responses fed back to a human input device coupled to the computer.

The foregoing has outlined various features of the invention so that those skilled in the pertinent art may better understand the detailed description of the invention that follows. Additional features of the invention will be described hereinafter that form the subject of the claims of the invention. Those skilled in the pertinent art should appreciate that they can readily use the disclosed conception and specific embodiment as a basis for designing or modifying other structures for carrying out the same purposes of the invention. Those skilled in the pertinent art should also realize that such equivalent constructions do not depart from the scope of the invention.

BRIEF DESCRIPTION OF THE DRAWINGS

For a more complete understanding of the invention, reference is now made to the following descriptions taken in conjunction with the accompanying drawings, in which.

DETAILED DESCRIPTION

One aspect of the invention is directed to a vision testing system that includes a computer, a display, and a human input device. The computer generates dynamic images with which the user interacts. By monitoring the user's responses, the system can diagnose vision conditions and track vision performance.

Figure 1:
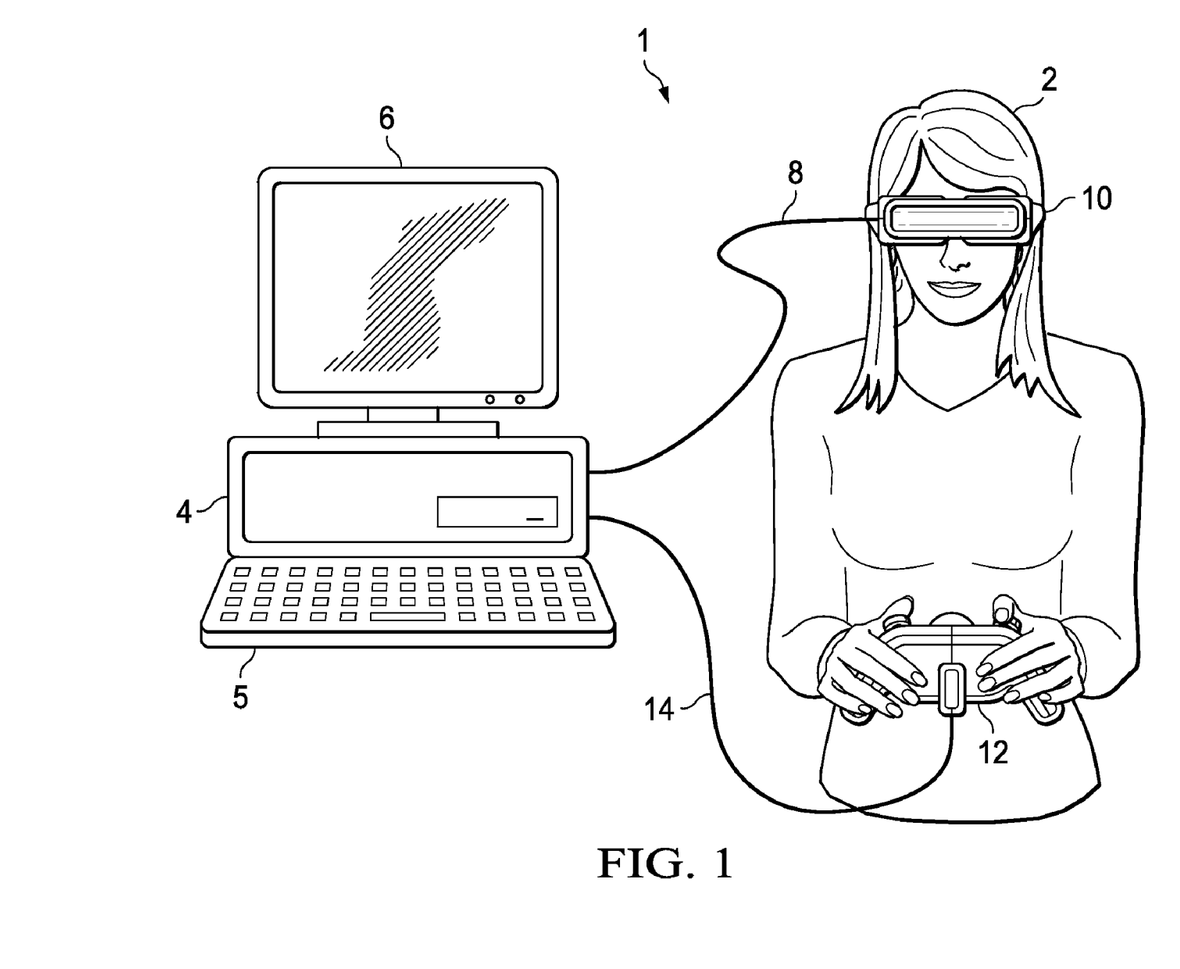
FIG. 1 shows a test subject undergoing a computerized vision test involving a computer with conventional display and keyboard, a head mounted binocular viewer, and a game controller.

In FIG. 1, a test subject 2 of a computerized vision testing system 1 is shown wearing a binocular viewer 10 connected by a display electrical cable 8 to a computer 4. The computer 4 generates a series of test images that are viewed on the binocular viewer 10 by the test subject 2 and depending on how the test subject 2 discerns the test images; the test subject 2 provides feedback through the game controller 12. The test subject may also provide feedback through the keyboard 5 and might also directly view test images on the conventional computer monitor 6. In this embodiment, it is desirable to make use of the binocular viewer 10 the benefits of which will be clear as the embodiment is described. The binocular viewer 10 is a binocular computer display device such as those commonly used in gaming and virtual reality systems. Later, additional embodiments using a conventional computer monitor 6 will be described. It is noted that the game controller 12 is shown connected to computer 4 through the controller electrical cable 14.

Of course, many possible variations exist on the preferred embodiment of the computerized vision testing system 1 shown in FIG. 1. For example, instead of using electrical cables, the binocular viewer 10 and game controller 12 could be connected wirelessly. Other human input devices instead of a game controller 12 or keyboard 5 could be employed such as a joystick, voice response system, computer mouse, foot pedals, touch-sensitive displays, or any of a multitude of other devices capable of allowing the test subject 2 to provide input to the computer 4. In fact, the computerized vision testing system 1 may be operated manually by an operator or technician in which case the test subject 2 might provide verbal feedback to the operator or technician so that no human input device need be directly operated by the test subject 2. The system is not shown with audio capability, but speakers either on the computer 4, built into the binocular viewer 10 or otherwise provided could allow the system to provide both visual and audio stimulation providing an enhanced experience for the test subject 2. The computerized vision testing system 1 might also provide vibration or other forms of stimulation to the test subject 2. And, of course, while a desktop computer is shown as the computer 4 in FIG. 1, the functions of the computer 4 could well be miniaturized and incorporated into the binocular viewer 10, or could be provided through some other device capable of providing the same computer functions. For example, a personal digital assistant (PDA), gaming console, notebook computer, or cell phone could possibly perform the function of the computer 4 in FIG. 1.

Operation of the computerized vision testing system 1 is similar to a computer game system. The computer 4 generates specific images that are viewed by the test subject 2 and the test subject's 2 responses are fed back to the computer 4 through the game controller 12. As a simple example, if a conventional eye chart (Snellen Chart) were shown on the binocular viewer 10, the test subject might indicate which letters they can read and which are not discernable. In this way, the computerized vision testing system 1 can assess basic vision function.

It is the goal of the computerized vision testing system 1 shown in FIG. 1 to screen the test subject 2 for vision disorders. To understand the benefit and specific operation of the system, it is helpful to recall the basic function of human vision. Light is processed through the focusing mechanism at the front of the eye (the lens and cornea) so that a substantially focused image falls on the retina. It is the function of the retina to convert the light stimulus falling on its surface into neurological signals that are passed to the brain via the optic nerve. The retina contains millions of photo sensors to achieve this goal. The sensors are sensitive to both light intensity and to color. The macula, or central region of the retina, contains the most dense concentration of photo sensors and is responsible for acute vision and detail. Hence, to accurately test the retinal function of the test subject 2, it is important to provide repeatable stimulus to specific areas of the test subject's 2 retina. The normally smooth and consistent retina surface is disrupted and becomes roughened and distorted with the onset of many retinal diseases, hence, it is also important to assess not only the ability of the photo sensors in the retina to function, but also to determine if distortion of the surface of the retina is causing distortion of the test subject's 2 vision function.

It should be clear, then, that the binocular viewer 10 can provide some benefit versus a conventional computer monitor 6 in testing for retinal disease. As the binocular viewer 10 is mounted to the test subject's 2 face, it can be consistently positioned relative to the test subject's 2 eyes and consistently map the function of the test subject's 2 retinas on repeated tests. Through automatic assessment of the test subject's 2 vision function, such as detection of the location of the natural blind spot of the test subject's 2 eyes, small misalignments can be automatically detected and compensated, while large misalignments can be signaled to the test subject 2 as a need to better align the binocular viewer 10. The use of binocular viewer 10 also allows the computer 4 to automatically sequence the test images so that they appear to only one of the test subject's 2 eyes at a given time so that each of the test subject's 2 eyes can be tested individually. Stereoscopic testing in which all or some portion of the test images appear to both the test subject's 2 eyes at the same time is also possible and will be discussed in more detail later.

Figure 2:
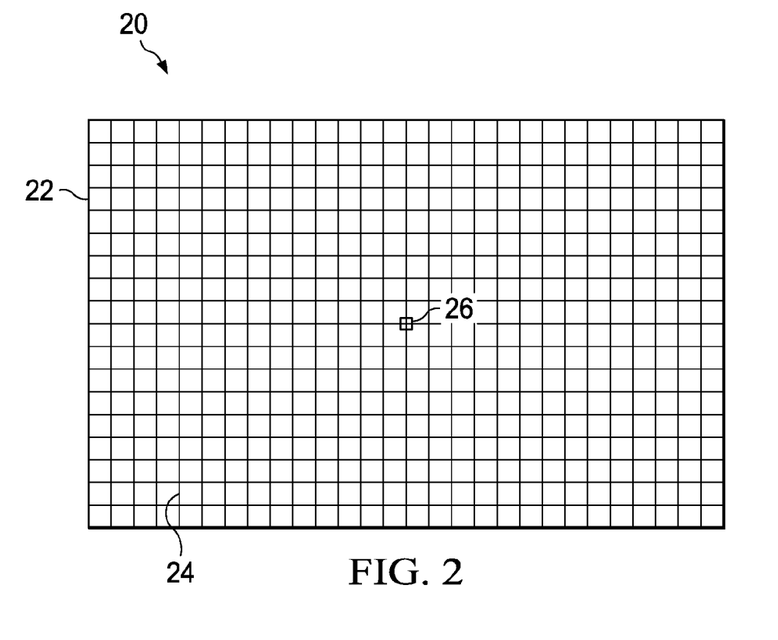
FIG. 2 shows an Amsler grid which can be displayed on a computer or can be simple paper or cardboard tests.

Now that the basic function of the computerized vision testing system 1 has been described, the type of testing images to be employed can be described. In FIG. 2, an Amsler grid 20 test image is shown. The grid is most commonly provided as a black grid printed on a piece of white paper or cardboard. In the case of a paper or cardboard Amsler grid 20, the test subject holds the grid at a comfortable distance (typically around arm's length) and with one eye covered, fixes their vision at the central feature 26. Without moving from his or her fixation from the central feature 26, the test subject views the grid sections 24 and notes if any of them are wavy, distorted, or missing. In this way, the Amsler grid 20 test is capable to test the basic operation of the photo sensors in the retina and also to provide a basic check on whether or not the retina has been distorted by disease. Note that the outer boundary 22 of the Amsler grid 20 limits the field of vision that can be covered in a given test, depending also on the size of the grid used and also on how far it is held from the test subject's 2 face during the test.

Of course, the Amsler grid 20 can also be displayed on a computer and, in particular, on the binocular viewer 10 of FIG. 1. In such a case, the outer boundary 22 would normally be limited by the viewing size of the binocular viewer 10. Providing an Amsler grid 20 test on a computerized vision testing system 1 provides many benefits. The color, brightness, contrast, grid size, and other possible features of the test can be varied to provide the best possible results. Also, testing of one of the test subject's 2 eyes versus the other can be automatically controlled by the computer 4. And as the perceived distance to the image is set by the optics in the binocular viewer 10, it is consistent and does not vary with how the test subject 2 holds a paper grid.

However, the Amsler grid 20 suffers from some basic problems. The first is that many test subjects may view the grid from different angles, in different light conditions, and at different distances, so that their personal assessment of whether the grid is distorted may be affected by many factors. Often times, test subjects will move the grid and may vary their point of fixation away from the central feature 26 to partially correct their vision. In this way, they can make small distortions in the grid less noticeable and claim good vision when problems exist. Clearly, such behavior by a test subject leads to false negatives that could have serious consequences.

False positive test results are also clearly possible with the Amsler grid 20. Small distortions in the printed grid or small errors due to lighting or other factors may cause the test subject to report problems when his or her vision is, in fact, perfectly normal. The expensive additional screening and examination needed to confirm no retinal disease is then wasted on a case where no problem should have been signaled from the beginning.

Figure 3:
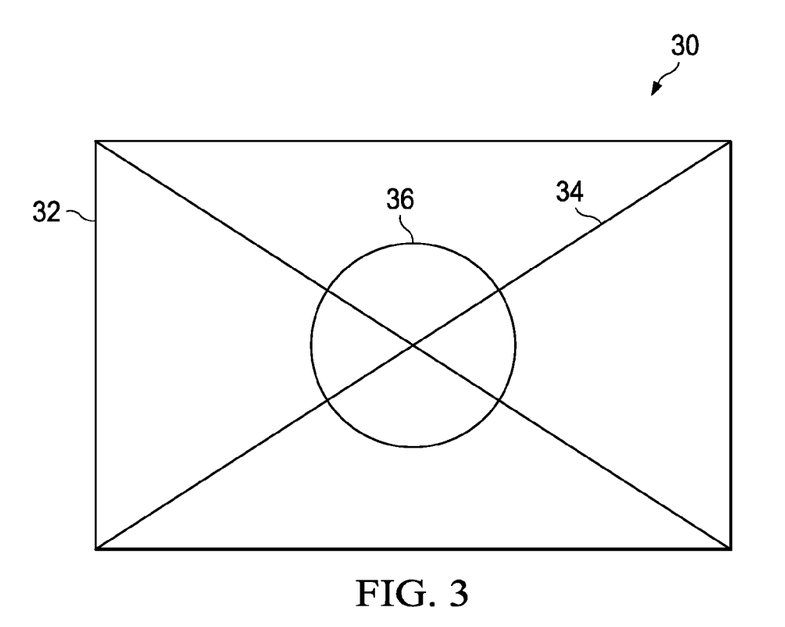
FIG. 3 shows a shape discrimination test image.

It is beneficial then, to consider other possible test images and to determine if other methods for testing can provide better results. In FIG. 3, a test image 30 using a circle 36 is provided. When implemented on the computerized vision testing system 1, the test subject 2, would view the circle 36 on the binocular viewer 10 with one eye (the system would automatically test only one eye at a time). The image viewed would include all the features shown in FIG. 3 inside the outer boundary 32 including the circle 36 and the cross hairs 34. Note that the cross hairs 34 are provided to create a central feature for fixation, the point where the diagonal cross hairs 34 intersect. Of course, other central features such as vertical and horizontal cross hairs, a central dot, or other possible features are possible. There is some benefit to using cross hairs for this, however, as test subjects 2 with severe central or peripheral vision loss, as may be caused by macular degeneration or glaucoma for example, can still fixate properly with their remaining vision function. The test image 30 using circle 36 is a very simple test. The test subject 2 simply views the circle 36 and reports to the computer 4 through the game controller 12 if the circle is smooth or distorted. Of course, there are some problems with using a simple circle 36 as a test image. Clearly, the circle 36 only tests the portion of the retina near where the circle falls, and distortion of the circle may be very hard to judge. A method to address these concerns is to introduce dynamic images and that will be described shortly.

Figure 4:
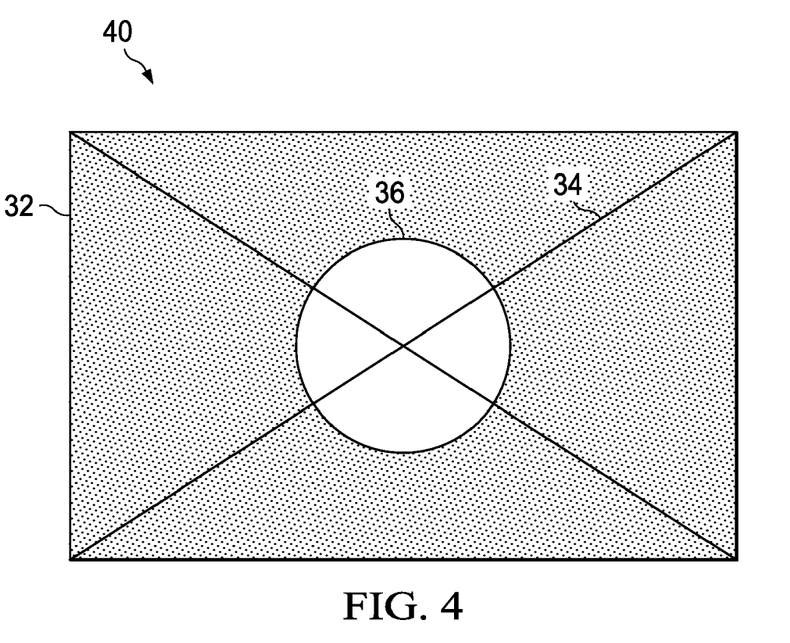
FIG. 4 shows a shape discrimination test image using a light central region and a darkened peripheral region.

Before dynamic images are described, note the test image 40 using a circle 36 and darkened outer region shown in FIG. 4. Here, the region inside the outer boundary 32 and outside the circle 36 is darkened to create higher contrast between the region inside the circle 36 and outside it. For some test subjects 2, this may create a more specific and sensitive test. Of course, when implemented on the computerized vision testing system 1, many possible combinations of color, brightness, contrast, shading, and other factors may be applied to create the most sensitive possible test.

Figure 5A:
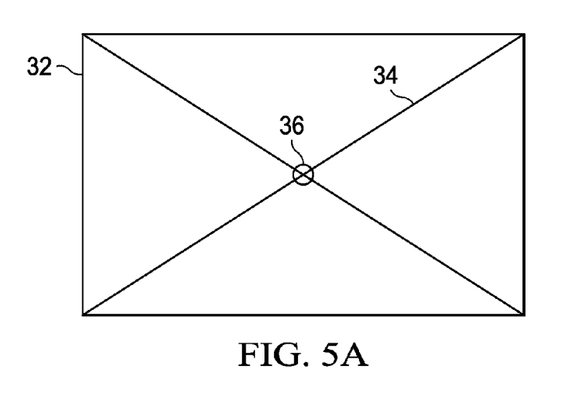
FIGS. 5A, 5B, 5C, and 5D show a sequence of images that could be found in dynamic shape discrimination testing.
Figure 5B:
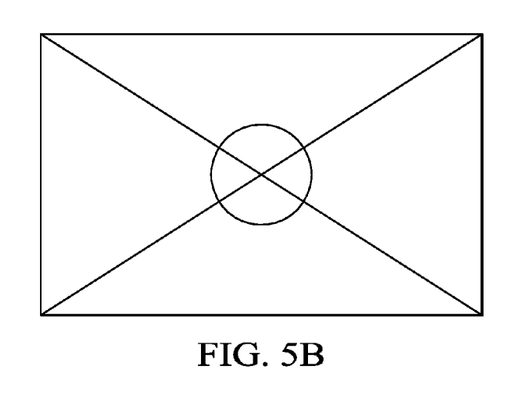
Figure 5C:
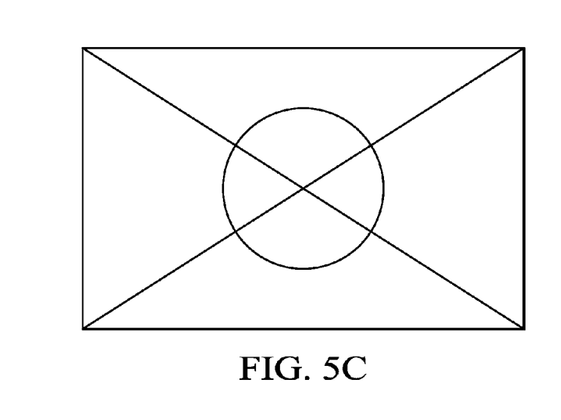
Figure 5D:
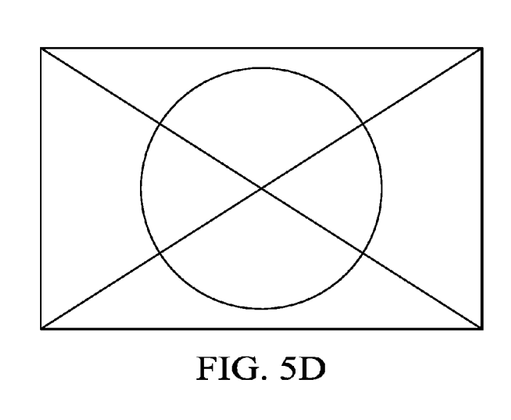

Now that test images using circles have been described, it is possible to explain how a dynamic image can offer benefit in retinal function testing. This is described in FIGS. 5A through 5D where a dynamic circle test is shown. In each of these figures, the test image 30 using a circle 36 of FIG. 3 is shown, but with the circle 36 of FIG. 3 at a different size. When using dynamic images, the circle 36 will start from a very small diameter circle, such as shown in FIG. 5A (it could also begin as a point and start expanding from there) and will smoothly and continuously increase in size becoming larger as in FIG. 5B, then as in FIG. 5C, and finally, to the largest possible size for the outer boundary, such as shown approximately in FIG. 5D. That is, the circle 36 will simply start out small and expand at some rate until it reaches maximum size at which point it will disappear (it could either abruptly disappear when a certain size is reached or it could extend smoothly until it is completely outside the outer boundary of the viewing area of the binocular viewer 10 or computer monitor 6).

In the dynamic circle test of FIGS. 5A through 5D, a key factor of the test is that the circle should expand at a rate that is sufficiently fast so that the test subject 2 is not able to move their point of vision fixation from the intersection of the cross hairs in the course of the test. This ensures that the full field of the retina within the field of view of the binocular viewer 10 is stimulated in sequence as the image of the circle passes over it. The test subject 2 is asked after the test has completed only if the circle appeared smooth and circular while it expanded. Since the image of the circle is symmetric about the fixation point and remains so as it expands, the test subject 2 is naturally inclined to keep his or her fixation constant through the course of the test. If the test subject 2 notices a ripple or distortion in the circle at some point as it expands, the computer 4 may initiate an input sequence that allows the test subject to indicate where in the display it was observed.

A key requirement for the dynamic circle test of FIGS. 5A through 5D is the rate at which the circle 36 expands. Clearly, if the expansion is very slow, the test subject 2 may be able to momentarily shift his or her point of fixation, reducing the accuracy of the test. And, if the expansion is very fast, the test subject may not have enough time to notice small distortions in the circle 36. As will be discussed later with regard to FIG. 6, it is possible with dynamic image testing to assess the test subject's ability to notice small distortions. In this way, the rate of expansion of the circle 36 can be automatically adapted to each particular test subject 2 so that optimal testing can be achieved. Of course, for some testing, it may not be desirable to undergo this automatic calibration before testing commences. And, even if automatic calibration is undertaken, it is necessary to begin the calibration process at a level consistent with typical vision function. Fortunately, it has been established in prior art that image changes taking place in less than roughly 200 milliseconds are sufficiently fast to avoid saccadic eye movement (rapid movement of the eye). Hence, testing with images changing in roughly 200 milliseconds or less should substantially avoid problems with the test subject 2 changing his/her vision fixation in the course of a test. This does not mean that the entire test sequence must be fully completed in less than 200 milliseconds. Rather, the requirement is only that sufficient change in the image occurs in less than roughly 200 milliseconds so that the test subject 2 is not able to move their point of fixation through saccadic eye movement.

The benefit of the dynamic test as described in FIGS. 5A through 5D should be clear. Versus an Amsler grid 20, the dynamic test provides substantial benefit as the testing time is contained and the test subject 2 is not allowed time to scan the image and vary their point of fixation. In this way, the test ensures that all possible regions of the retina are examined and that the test subject 2 does not move their point of fixation to reduce or eliminate distortion of the circle.

Figure 6:
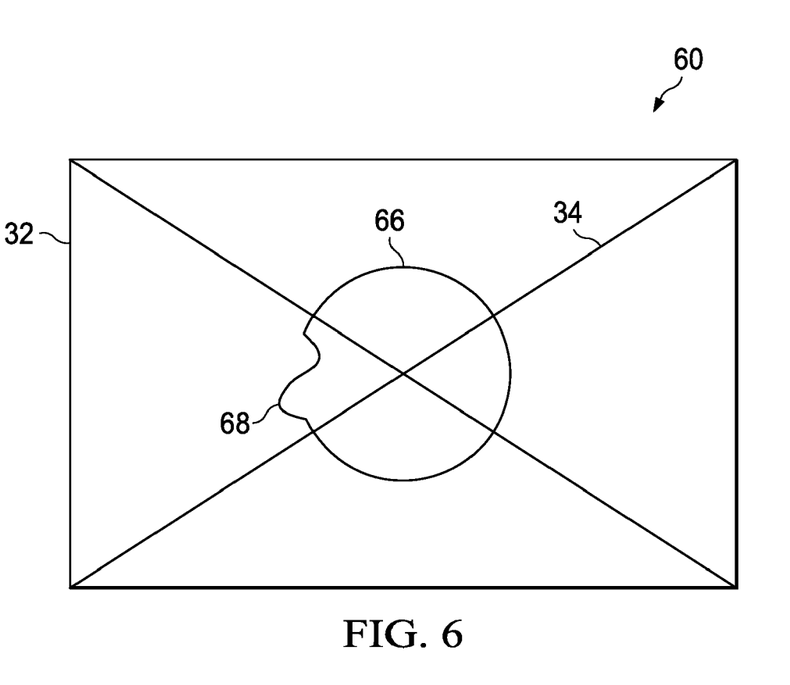
FIG. 6 shows a shape discrimination test image that includes a modulated section.

It is also possible to intentionally introduce distortions into the circle used for dynamic tests. As shown in FIG. 6, a modulated circle 66 can be formed from a regular circle with the addition of a modulated section 68. Note that the other features of the modulated circle test image 60 in FIG. 6, including the cross hairs 34 and outer boundary 32 are the same as those of FIGS. 3, 4, and 5A-5D. Introduction of a modulated circle 66 offers a new element to be added to a dynamic shape discrimination vision test. As the modulated circle 66 expands in a dynamic test, the distorted section 68 may be present for the entire time the modulated circle 66 is expanding or may only be present for some subset of the time the test is running. The modulated section 68 may also be placed at any angle around the modulated circle 66 (top, bottom, left, right, upper left, etc.). In fact, the entire circumference of the modulated circle 66 may be modulated, that is, the modulated section 68 could contain the entire circumference. The modulated section 68 may also be of any desired amplitude (amplitude is taken here as the difference between the maximum and minimum radius from any point on the modulated section 68 to the modulated circle 66 center, the point where the cross hairs 34 cross). Also, while the modulated section 68 in FIG. 6 is shown as a smooth modulating curve, other modulations such as triangular, square, or other sorts of modulations may be applied. Combinations of modulations and varying amplitudes of modulation as a function of circumference position are also possible. And finally, the spatial frequency of the modulation can also be varied. That is, the number of cycles of modulation that occur in a given length of arc along the modulated circles 66 circumference can also be varied.

With the addition of the modulated section 68, the test sequence the test subject 2 experiences can include an intentional modulation of the circle 66 at any location and size that is beneficial for the testing. That is, the test subject 2 can be tested both on their perception that a smooth and undistorted circle appears to be smooth and undistorted; and also in their ability to notice distortions that are placed in the circle intentionally by modulating the image (the convention is followed here that images are modulated in their construction, but the test subject notices them as distortions in the testing). This allows the computerized vision testing system 1 to determine if the test subject 2 can notice a distortion if it occurs and what level of distortion they can perceive. If the test subject 2 is not able to recognize large and obvious distortions intentionally introduced in the modulated circle 66, their vision may not be clear (or the test for some reason may not be operating properly) and other testing (such as directly scanning the retina with a diagnostic camera) may be required for that specific test subject 2. However, if the test subject 2 can consistently detect intentional distortions from the modulated circle 66 that are of a sufficiently small amplitude, then it is clear that their basic vision function is suitable to produce a correct and accurate result in the dynamic testing.

As explained above, the use of a modulated circle 66 for dynamic testing also allows automatic adjustment of how rapidly the modulated circle 66 expands in a dynamic test. Several tests may be run to assess the minimum amplitude of modulation a given test subject can perceive when the image is expanded very slowly or even kept at a constant size. Then, the rate of expansion can be increased until the test subject 2 can no longer accurately report distortion corresponding to the intentional modulation. This provides a measure of how fast the modulated circle 66 may be allowed to expand without compromising test accuracy.

It is clear that additional sensitivities of the test subject 2 can be measured with the modulated circle test image 60. For example, changes in the test subject's 2 ability to detect distortion due to modulation of the circle 66 in response to brightness, contrast, color, line weight, viewing time, and other factors can all be determined. In addition, the test subject's ability to accurately assess distortion due to the modulated section's 68 size, amplitude, shape, position, spatial frequency and other characteristics can also be determined.

It is noted that a key benefit of the test image using a circle 30 and the dynamic test shown in FIGS. 5A-5D is that the test image remains symmetrical about the central point of fixation (where the cross hairs 34 cross). Clearly, when the modulated circle 66 of FIG. 6 is introduced, the test image is no longer strictly symmetrical about the central point of fixation and when the modulated circle 66 is used in a dynamic test, the level of symmetry may change in the course of the test. However, the modulated circle 66 does provide a level of symmetry that makes it preferable to other possible tests such as the Amsler grid 20. Consequently, while not perfectly symmetric, the modulated circle 66 is sufficiently symmetric to offer benefit.

Another embodiment of the invention uses conventional computer display 6 shown in FIG. 1 instead of the binocular viewer 10. The techniques of this invention are largely unchanged using a conventional computer display 6 if: (1) test subject 2 is kept at a suitable distance from conventional display 6 to allow for comfortable viewing; (2) the size of conventional display 6 maps to the retina of test subject 2 so that the display covers a substantial view of a vision field of test subject 2; and (3) if test subject 2 undergoes testing with one eye covered with a patch or other device to allow only one eye to see at a time. Of course, movement of the test subject's 2 head relative to the conventional display 10 and lack of precise alignment may make the testing somewhat less accurate. However, in the case that no binocular viewer 10 is available, testing with a conventional display 6 allows many of the benefits of shape discrimination testing with dynamic images to still be gained.

Another embodiment of the invention is to use the stereoscopic viewing capability of the binocular viewer 10. That is, with both eyes seeing images at the same time, the binocular viewer 10 is capable to deliver a stereoscopic image. Testing in this manner may be more comfortable for some test subjects 2 as normal human vision experience is already stereoscopic. In stereoscopic testing, modulations of the test image, such as the modulated section 68 in FIG. 6, can be applied to either one eye at a time or to both eyes at the same time. If the modulation is applied to only one eye, the ability of the test subject 2 to detect the associated distortion in the test image can be assessed individually for each eye. Features displayed to both eyes can provide a consistent image that is comfortable to view. Stereoscopic testing also opens the opportunity to use 3-dimensional stereoscopic images for testing. That is, instead of viewing circles, the test subject 2 could be shown spheres that may or may not include modulated sections.

Many simple variations of the tests using dynamic images can also be envisioned. For example, in FIGS. 5A through 5D, the circle 36 started out very small and was enlarged dynamically. Clearly, the sequence could be reversed. That is, the circle 36 could start out large and shrink dynamically to a very small circle or point. Such a change could be offered to the test subject 2 as a preference in the testing. Also, for some test subjects 2, this difference could be substantial. For example, a test subject 2 with severe central vision loss may benefit from a test in which a large circle is shrunk since the starting image would be visible in their peripheral vision. Conversely, a test subject with peripheral vision loss may benefit from a small circle that is expanded as shown in FIGS. 5A-D. Of course, variations in the color, brightness, contrast, line weight, and other aspects of both the circle 36, background, and cross hairs 34, are possible.

Figure 7:
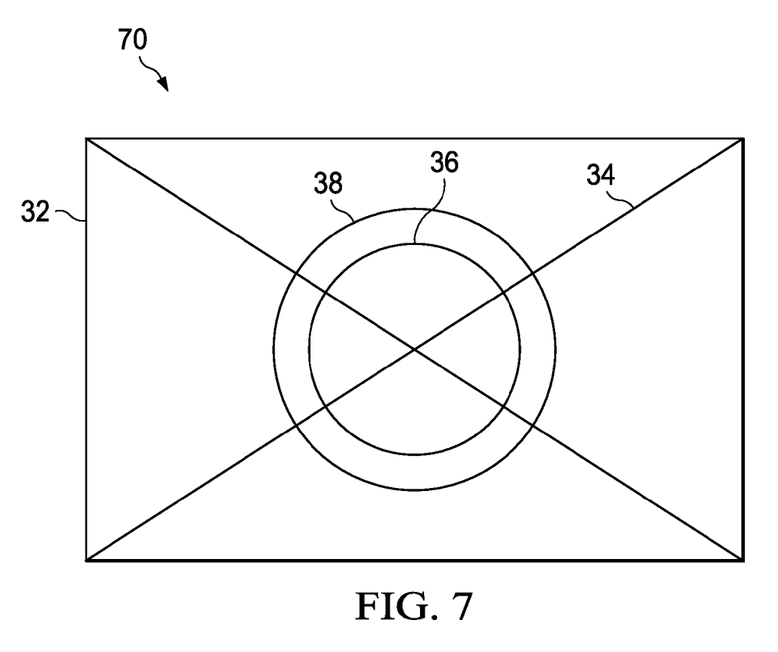
FIG. 7 shows the shape discrimination test image of FIG. 3 with the addition of a companion image.

FIG. 7 illustrates an embodiment of the invention where a companion circle 38 is introduced into the dynamic shape discrimination vision testing. Circle 38 is drawn with a close and consistent separation from the original circle 36 so that one circle is inscribed inside the other. Some form of consistent separation is then maintained as the dynamic image is expanded or shrunk (it may be a dimensionally constant difference in the radius of the two circles, a constant proportion of the radius of either circle, or may vary as the circles expand or contract due to some other beneficial formula). By providing a companion circle 38, it is possible to make distortions in the circle 36 more easily detectable and result in a more precise test. Of course, multiple companion circles that may be either larger or smaller than the circle 36 are possible.

Figure 8:
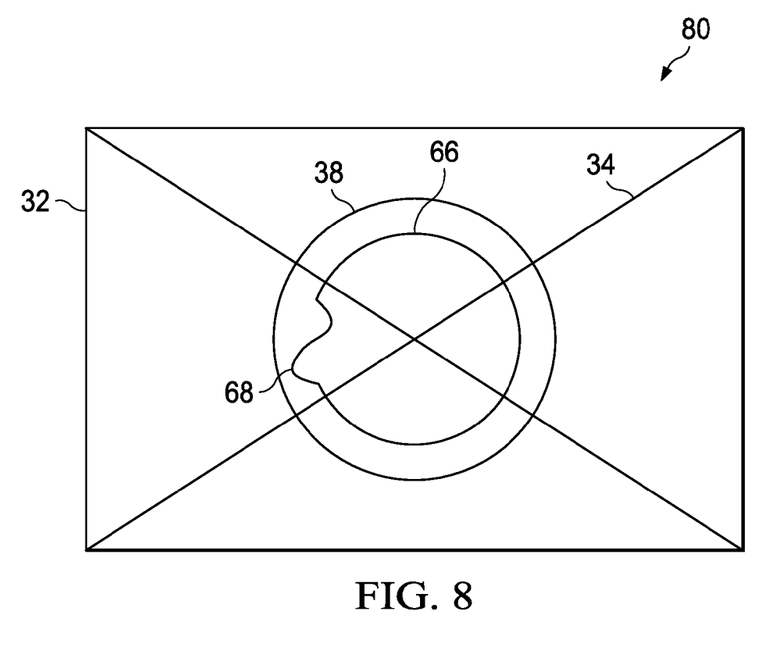
FIG. 8 shows the shape discrimination test image that includes the modulated section of FIG. 6 with the addition of a companion image.

FIG. 8 shows a companion circle 38 with a modulated circle 66 having modulated section 68. As in FIG. 7, the companion circle 38 provides a visual reference to make any distortion seen by the test subject 2 in the modulated circle 66 more easily visible. In FIG. 8, the modulated section 68 is used as described previously with regard to FIG. 6, but with the benefit of a companion circle 38. As with FIG. 7, multiple companion circles are also possible.

Figure 9:
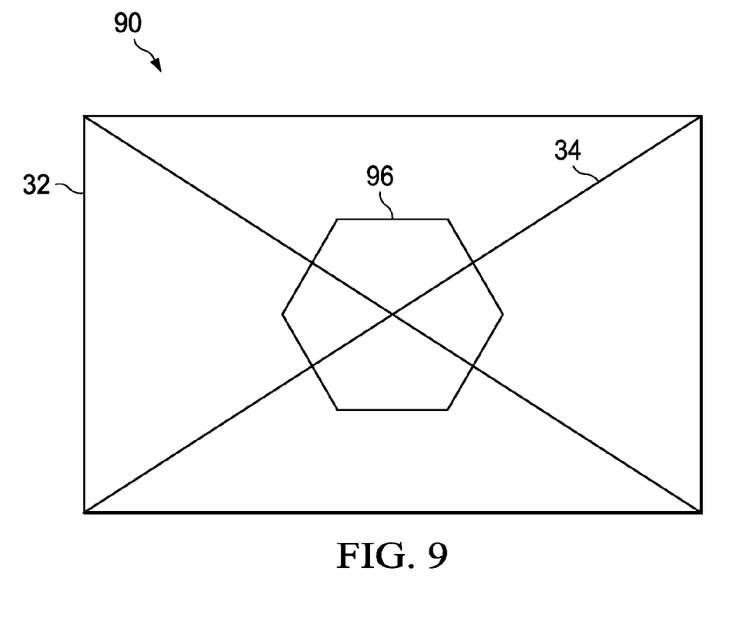
FIG. 9 shows a shape discrimination test image that is a hexagon.

FIG. 9 illustrates an embodiment of the invention where figures other than circles can be used for dynamic image testing. In FIG. 9, a hexagon 96 is used in a dynamic test image 90. Many possible test images including triangles, rectangles, trapezoids, octagons, and many other possible images may be used. Of course, modulated sections and companion images may be applied to them in similar fashion to the description above for the use of circles. It is noted that in addition to expanding about a central point of fixation, figures other than circles could also be rotated in the course of a test. In this way, additional regions of the retina could be tested. And, of course, while some of these images are not perfectly symmetrical, many possible images that are sufficiently symmetrical to be adequate for vision testing are possible.

Figure 10:
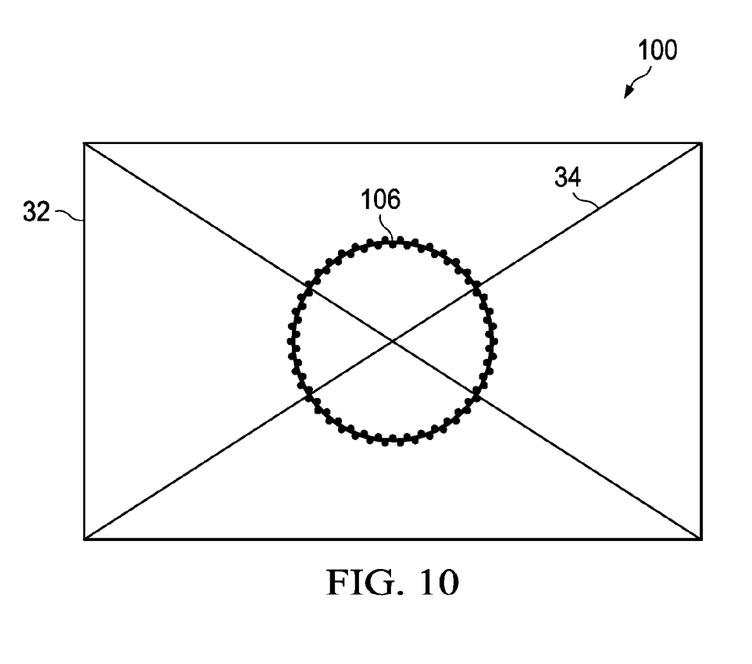
FIG. 10 shows a shape discrimination test image including textured lines.

In FIG. 10, a circle test image with texturing 100 is shown. The textured circle 106 is formed from a textured line instead of a sharp line as in the previous figures. Variations in line weight, texture, illumination, sharpness, and many other aspects can be varied. Texturing can provide benefit in some testing as it may be more challenging for a test subject 2 to perceive a slightly fuzzy image versus a very sharp one. In this way, the texturing forces the test subject to view the test image as a full shape and not to only concentrate on some specific features of the image and only track them.

Figure 11:
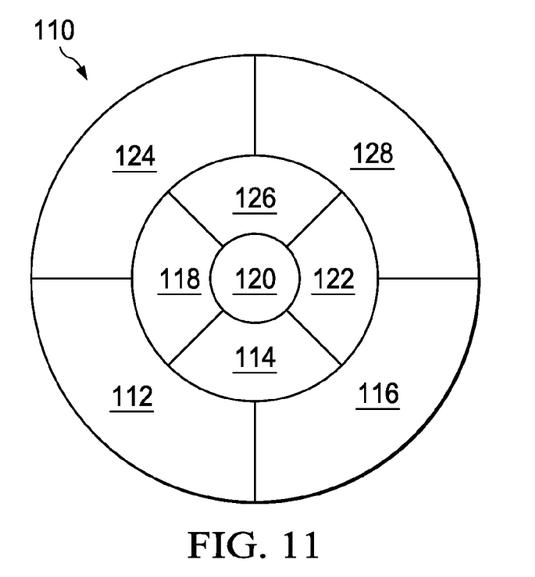
FIG. 11 shows an image with defined regions.

In FIG. 11, an image with defined regions 110 is shown. The defined regions include the lower left outer section 112, bottom inner section 114, lower right outer section 116, left inner section 118, center section 120, right inner section 122, upper left outer section 124, top inner section 126, and upper right outer section 128. The image with defined regions 110 may be used to categorize the location in which a test subject 2 observes distortion or loss of vision, or where retinal disease is found on a retinal photograph corresponding to the defined regions. In vision testing with dynamic images, it is possible to determine, as previously described, where a test subject 2 observes distortion of his or her vision. This information can then be categorized into regions of the image with defined regions 110, or can be categorized in other possible ways. Of course other images with defined regions, such as, e.g., a rectilinear grid could be used.

Figure 12:
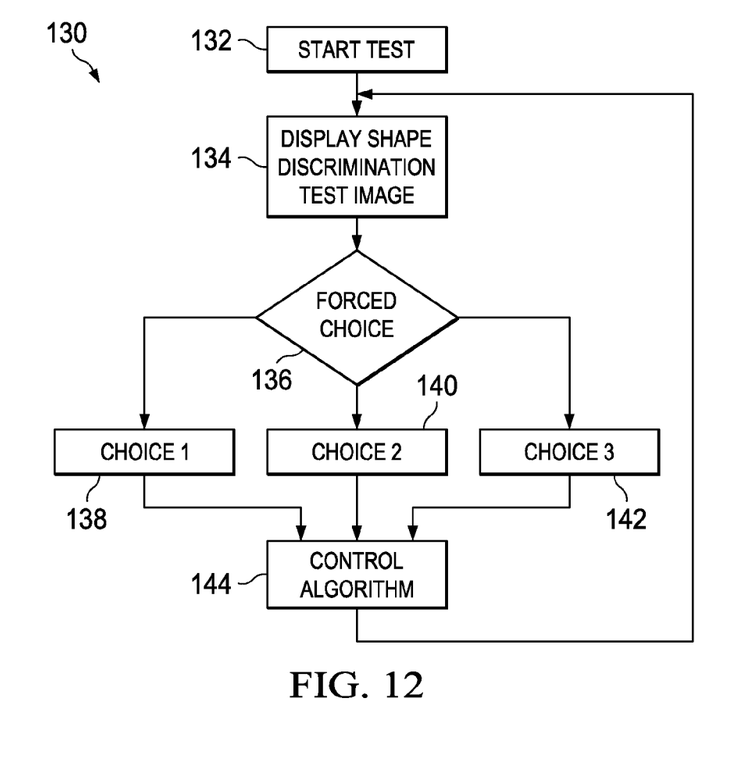
FIG. 12 shows a flow chart for a forced choice vision test.

FIG. 12 shows a flow chart for a vision test using forced choice control 130. It is noted that in some vision testing, the test subject 2 is only asked to report distortion if they observe it. For example, in Amsler grid 20 testing, the test subject only reports distortion if they notice it. By contrast, forced choice testing demands that for each image shown, the test subject 2 must make a choice. This allows a much more specific test to be created as the test subject cannot pass on certain questions or hide their inability to distinguish between images. As an example, in testing with the modulated circle of FIG. 6, the modulated section 68 could appear anywhere and at any amplitude (including no modulation at all). So a test subject 2 with retinal damage in an area of his or her vision should not be able to substantially distinguish between a modulated and not-modulated test image in that damaged region of vision. While in some tests the test subject 2 may be able to hide this inability, if the test subject 2 is forced to make a choice as to whether a first or second image is modulated, their inability to accurately do so becomes clear.

In the flow chart for a vision test using forced choice control 130, the operation of a forced choice vision test is provided. The start test 132 block includes all the operations needed to power up the system and provide the first test image. The display shape discrimination test image 134 block includes the operations needed to actually display the test image for the test subject 2 to observe. With regard to FIG. 12, the test image may be either static or dynamic. The forced choice 136 block represents the choice the test subject 2 must make to allow the testing to progress. Note that multiple choices may be possible and could be of any number, but that three possible choices, choice 1 138, choice 2 140, or choice 3 142 are shown as possible choices in FIG. 12. The test subject 2 is forced to choose one of these. For example, choice 1 138 may be that a first image is more clear, choice 2 140, may be that a second image is more clear, and choice 3 142 may be that a third image is more clear. The test subject 2 makes a choice and the corresponding block sends a logical signal to the control algorithm 144 which, in turn, determines the course of the testing and the next test image to be displayed.

Figure 13:
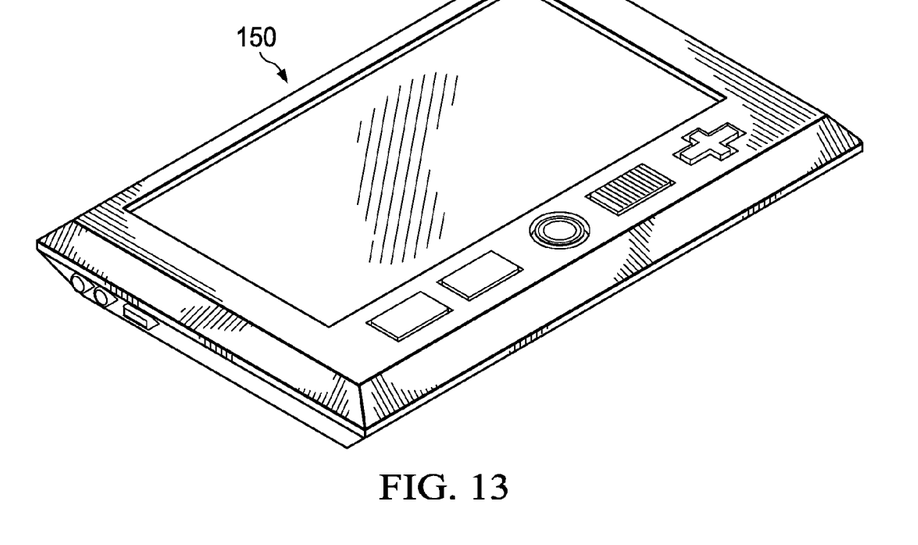
FIG. 13 shows a handheld touch sensitive display.

In order to aid test subject 2 with making these forced choices, the display 6 of computerized testing system 1 could be replaced with a handheld touch-sensitive display 150 as illustrated in FIG. 13 where test subject 2 may select choices by touching a specific area on the touch-sensitive display.

Figure 14:
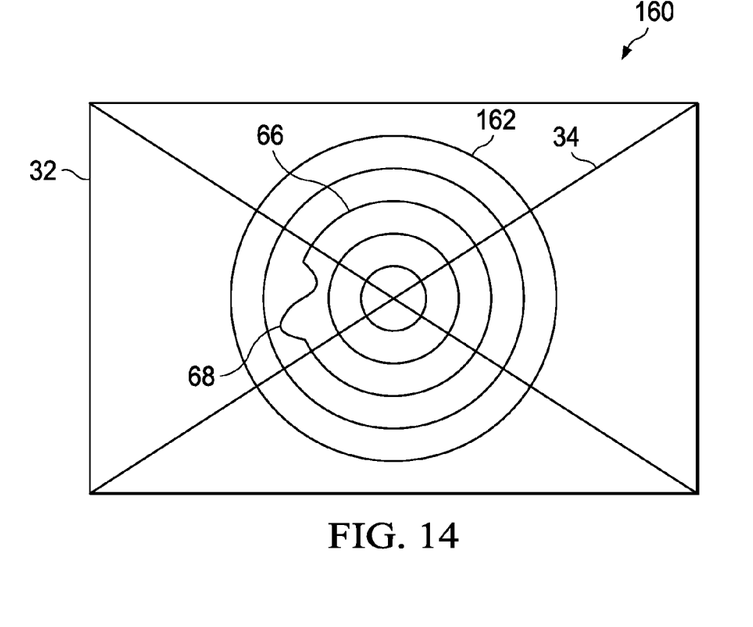
FIG. 14 shows a static image with multiple circles.

It is also possible to use the techniques of this invention to allow improved testing with static images. As was noted previously, a drawback with the Amsler grid 20 is that the test subject 2 may move their point of fixation and scan the grid, leading to erroneous results. Using the image of concentric circles 160 as shown in FIG. 14, this can be made less likely by choosing an image, in this case concentric circles, that make the test subject 2 less likely to vary his or her point of fixation away from the center of the image. It is noted that a modulated section 68 may be applied to one of the concentric circles 162 to create a modulated circle 66 as was first described with regard to FIG. 6. In the test image of concentric circles 160, the image is static and does not expand or contract. However, it may be displayed only briefly so that the test subject 2 is not given time to vary their point of fixation and scan the image. That is, it may only be displayed for a few hundred milliseconds. Of course, the cross hairs 34 could be displayed continuously so that a fixed point of fixation is established before the concentric circles 162 are displayed and then blanked. Of course, other test images such as concentric triangles, squares, hexagons, octagons, and many other shapes could be used instead of the circles shown in FIG. 13.

The benefits of the present invention should be clear. It offers techniques to allow for automatic testing of vision function through shape discrimination of dynamic images. Compared to legacy screening tools such as the Amsler Grid, computerized screening with dynamic images ensures that inconsistent points of fixation don't result in erroneous tests. Additionally, the benefits of using a computer system to improve test repeatability, ensure proper test sequences, ensure valid results, analyze and store results, and other benefits are obtained. These dynamic image tests can include many different shapes and configurations and can operate with conventional computer displays, with binocular viewers, or with other types of computer displays. Vision function testing with dynamic images can be used for disease screening, detecting injury, and for tracking the status of disease in a test subject already diagnosed with disease or injury.

Those skilled in the art to which this application relates will appreciate that other and further additions, deletions, substitutions and modifications may be made to the described embodiments.

What is claimed is:

1. A vision testing system, comprising:
a display,
a computer coupled to said display and configured to provide dynamic images, each including a point of fixation, wherein each of said dynamic images is a substantially closed shape expanding or contracting substantially symmetrically about said point of fixation; and
a human input device coupled to said computer, wherein responses from a test subject are fed back to said computer to assess said test subject's vision function.

2. The system as recited in claim 1, wherein said display is a binocular viewer.

3. The system as recited in claim 1, wherein said test subject input device is selected from the group consisting of: a keyboard, a game controller, a joystick, a voice response system, a computer mouse, and foot pedals.

4. The system as recited in claim 1, wherein said system is operated manually by an operator or technician based on verbal feedback from said test subject.

5. The system as recited in claim 1, wherein said point of fixation is an intersection of crosshairs.

6. The system as recited in claim 1, wherein a rate of change of said expansion or contraction is such that there is a sufficient change in said at least one of said dynamic images in less than an about 200 milliseconds.

7. The system as recited in claim 1, wherein at least one of said dynamic images includes a modulated section.

8. The system as recited in claim 7, wherein said at least one of said dynamic images is a circle.

9. The system as recited in claim 7, wherein said at least one of said dynamic images includes said modulated section for a portion of a duration of said at least one of said dynamic images.

10. The system as recited in claim 1, wherein said dynamic images are presented to only one eye of said test subject at a time.

11. The system as recited in claim 1, wherein at least one of said dynamic images contains multiple similar companion shapes, each of said companion shapes expanding or contracting substantially symmetrically from said point of fixation.

12. The system as recited in claim 11, wherein at least one of said multiple similar companion shapes includes a modulated section.

13. The system as recited in claim 1, wherein at least one of said dynamic images includes at least one defined region to allow said test subject to identify distortion in said at least one defined region.

14. The system as recited in claim 1, wherein said test subject is forced to choose one of a multiple of said dynamic images presented that appears to be the most clear dynamic image.

15. A method to assess vision function, comprising:
providing dynamic images, each including a point of fixation, to a test subject on a display coupled to a computer, wherein each of said dynamic images is a substantially closed shape expanding or contracting substantially symmetrically about said point of fixation; and
assessing said test subject's vision function based on responses from said test subject while viewing said dynamic images, said responses fed back to a human input device coupled to said computer.

16. The method as recited in claim 15, wherein said display is a binocular viewer.

17. The method as recited in claim 15, wherein said input device is selected from the group consisting of: a keyboard, a game controller, a joystick, a voice response system, a computer mouse, and foot pedals.

18. The method as recited in claim 15, wherein said responses are verbally given to an operator or technician who operates said input device.

19. The method as recited in claim 15, wherein said point of fixation is an intersection of crosshairs.

20. The method as recited in claim 15, wherein a rate of change of said expansion or contraction is such that there is a sufficient change in said at least one of said dynamic images in less than an about 200 milliseconds.

21. The method as recited in claim 15, wherein at least one of said dynamic images includes a modulated section.

22. The method as recited in claim 21, wherein said at least one of said dynamic images is a circle.

23. The method as recited in claim 21, wherein said at least one of said dynamic images includes said modulated section for a portion of a duration of said at least one of said dynamic images.

24. The method as recited in claim 15, wherein said dynamic images are presented to only one eye of said test subject at a time.

25. The method as recited in claim 15, wherein at least one of said dynamic images contains multiple similar companion shapes, each of said companion shapes expanding or contracting substantially symmetrically from said point of fixation.

26. The method as recited in claim 25, wherein at least one of said multiple similar companion shapes includes a modulated section.

27. The method as recited in claim 15, wherein at least one of said dynamic images includes at least one defined region to allow said test subject to identify distortion said at least one defined region.

28. The method as recited in claim 15, wherein said test subject is forced to choose one of a multiple of said dynamic images presented that appears to be the most clear dynamic image.

* * * * *